(12) United States Patent
Stenzler et al.

(10) Patent No.: US 9,010,321 B2
(45) Date of Patent: Apr. 21, 2015

(54) BACTERIA FILTER AND HEATING SYSTEM

(75) Inventors: Alex Stenzler, Long Beach, CA (US); Steve Han, Huntington Beach, CA (US)

(73) Assignee: 12th Man Technologies, Inc., Garden Grove, CA (US)

( * ) Notice: Subject to any disclaimer, the term of this patent is extended or adjusted under 35 U.S.C. 154(b) by 649 days.

(21) Appl. No.: 13/328,602

(22) Filed: Dec. 16, 2011

(65) Prior Publication Data

US 2013/0152929 A1   Jun. 20, 2013

(51) Int. Cl.
*A62B 7/10* (2006.01)
*A62B 19/00* (2006.01)
*A62B 23/02* (2006.01)
*F24J 3/00* (2006.01)
*A61M 16/10* (2006.01)

(52) U.S. Cl.
CPC ....... *A61M 16/1055* (2013.01); *A61M 16/1095* (2014.02); *A61M 16/1075* (2013.01); *A61M 2205/3653* (2013.01); *A61M 2205/584* (2013.01); *A61M 2205/7509* (2013.01); *A61M 2205/7518* (2013.01); *A61M 2205/7536* (2013.01); *A61M 16/1065* (2014.02)

(58) Field of Classification Search
CPC .......... A61M 16/105; A61M 16/1055; A61M 16/106; A61M 16/1065; A61M 16/1075; A61M 16/108; A61M 16/1085; A61M 16/109; A61M 16/1095; A61M 16/1045; A61M 2205/7518; A61M 2205/7536; A61M 2205/36
USPC ............. 128/200.24, 204.17, 201.13, 201.25, 128/203.26, 203.27, 205.15, 205.27, 128/205.29; 55/490.1, 490.2; 95/283
See application file for complete search history.

(56) References Cited

U.S. PATENT DOCUMENTS

| | | | |
|---|---|---|---|
| 4,172,709 A * | 10/1979 | Kippel et al. | 96/416 |
| 4,678,488 A * | 7/1987 | Howard et al. | 55/406 |
| 4,727,871 A | 3/1988 | Smargiassi et al. | |
| D344,586 S | 2/1994 | Choate | |
| 5,660,171 A * | 8/1997 | Kimm et al. | 128/204.23 |
| 5,906,201 A * | 5/1999 | Nilson | 128/203.16 |
| 6,170,684 B1 * | 1/2001 | Vincent et al. | 215/261 |
| 6,220,245 B1 | 4/2001 | Takabayashi et al. | |
| 6,619,287 B2 | 9/2003 | Blackhurst et al. | |
| 7,497,215 B1 | 3/2009 | Nguyen et al. | |
| 7,926,485 B2 | 4/2011 | Nguyen et al. | |
| 8,414,682 B2 * | 4/2013 | Larsen et al. | 95/25 |
| 2004/0236243 A1 * | 11/2004 | Eckerbom | 600/532 |
| 2008/0294090 A1 * | 11/2008 | Heath | 604/26 |

FOREIGN PATENT DOCUMENTS

GB   2277689 A  * 11/1994   ............ A61M 16/00

* cited by examiner

*Primary Examiner* — Lynne Anderson
*Assistant Examiner* — Bradley Philips
(74) *Attorney, Agent, or Firm* — Riverside Law LLP

(57) ABSTRACT

A system for keeping moisture in a vapor phase and for removing particles from a gas is described. The system includes a filter and a heating chamber. The filter is capable of being heated and includes a mechanical element that effectively regulates the heating of the filter. Heat production of the heating chamber is coupled to the proper insertion of the filter into the chamber, such that the filter closes an electrical switch in the heating chamber to allow for the production of heat. An exemplary use of the system is the keeping moisture in a vapor phase and removing pathogenic particles from the exhalation path of a ventilated subject.

11 Claims, 7 Drawing Sheets

BACTERIA FILTER AND HEATING SYSTEM

BACKGROUND OF THE INVENTION

Ventilator systems provide necessary assistance in the breathing of sick or otherwise compromised patients who cannot adequately breathe on their own. Generally, ventilation systems include an inhalation path that brings air to the patient and an exhalation path that takes exhaled air away from the patient. An important consideration in the use of ventilator systems is the need for proper care of the exhaled gas in the exhalation path.

Exhaled gas from a sick patient can contain bacteria, viruses, and other small particulates ("pathogens") that can contaminate the surrounding air. Further, exhaled gas contains considerable moisture which can cool and condense in the exhalation path. The buildup of condensed moisture in the exhalation path can damage the electrical and mechanical circuitry of vital components of the ventilator system.

These issues have led to the incorporation of filters into the exhalation path to remove pathogens from exhaled air. However, while these filters can effectively remove pathogens, they cannot on their own combat the ultimate buildup of condensed moisture. Thus, in these types of ventilator systems, the exhalation path components, including the filter, must be periodically cleaned and sterilized or replaced. Other ventilator systems have since been developed to include an internal heating mechanism that heats the filter. By heating the filter, the moisture in the exhaled gas is mostly kept in vapor phase, thereby protecting the various components from condensed moisture based damage and further reducing potential from contamination. However, in these heated filter systems, the heating element, because it is internal to the ventilator, is powered and controlled separately from the filter. However not all ventilators have heated filters. Existing external heated filters create a potential risk when the filter is removed, exposing the operator to high surface temperatures of the heater body.

Therefore, there is a need in the art for a heated filter and filtration system, wherein control of the heating element can be effectively determined by the presence of the filter. The present invention satisfies this need.

SUMMARY OF THE INVENTION

The present invention includes a filter for removing pathogens and other small particles from a gas while keeping the moisture in a vapor phase. The filter includes a housing having a first opening and a second opening to create a passage therethrough, a filter medium contained within the housing and between the first opening and the second opening, such that a gas must pass through the filter medium along the passage, and a mechanical extension extending from the housing. In one embodiment, the mechanical extension closes an electrical switch. In another embodiment, the filter is sized and shaped to fit within a heating chamber. In another embodiment, the filter is heated when the mechanical extension engages and closes a recessed electrical switch within the heating chamber. In another embodiment, the mechanical extension is a ring. In another embodiment, the mechanical extension is plastic. In another embodiment, the filter is a HEPA filter. In another embodiment, the filter is a bacterial filter for a ventilator. In another embodiment, the gas is an exhaled gas from a ventilated subject.

The present invention also includes a system for keeping moisture in a vapor phase and removing particles from a gas. The system includes a heating chamber having a heating component and an electrical switch, a filter having a housing that includes a mechanical extension extending from the housing, wherein the filter is sized and shaped to engage the heating chamber, and wherein, when the filter engages the heating chamber, the mechanical extension closes the electrical switch of the heating chamber to activate heating of the filter. In one embodiment, the mechanical extension is a ring. In another embodiment, the heating component comprises a heating element and a heat transfer plate. In another embodiment, the filter is heated between about 40° C. and 60° C. In another embodiment, the filter is a HEPA filter. In another embodiment, the filter is a bacterial filter for a ventilator. In another embodiment, the gas is an exhaled gas from a ventilated subject.

The present invention also includes a method for keeping moisture in a vapor phase and removing particles from a gas. The method includes the steps of providing a heating chamber having a heating component and an electrical switch, providing a filter having a housing that includes a mechanical extension extending from the housing, wherein the filter is sized and shaped to engage the heating chamber, engaging the filter with the heating chamber, such that the mechanical extension closes the electrical switch of the heating chamber to activate heating of the filter, and administering a gas to the filter when the filter is heated, such that moisture is kept in a vapor phase or particles in the gas are captured in the filter. In one embodiment, the method further includes heating the filter between about 40° C. and 60° C. In another embodiment, the filter is a HEPA filter. In another embodiment, the gas is an exhaled gas from a ventilated subject.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION

Figure 1:
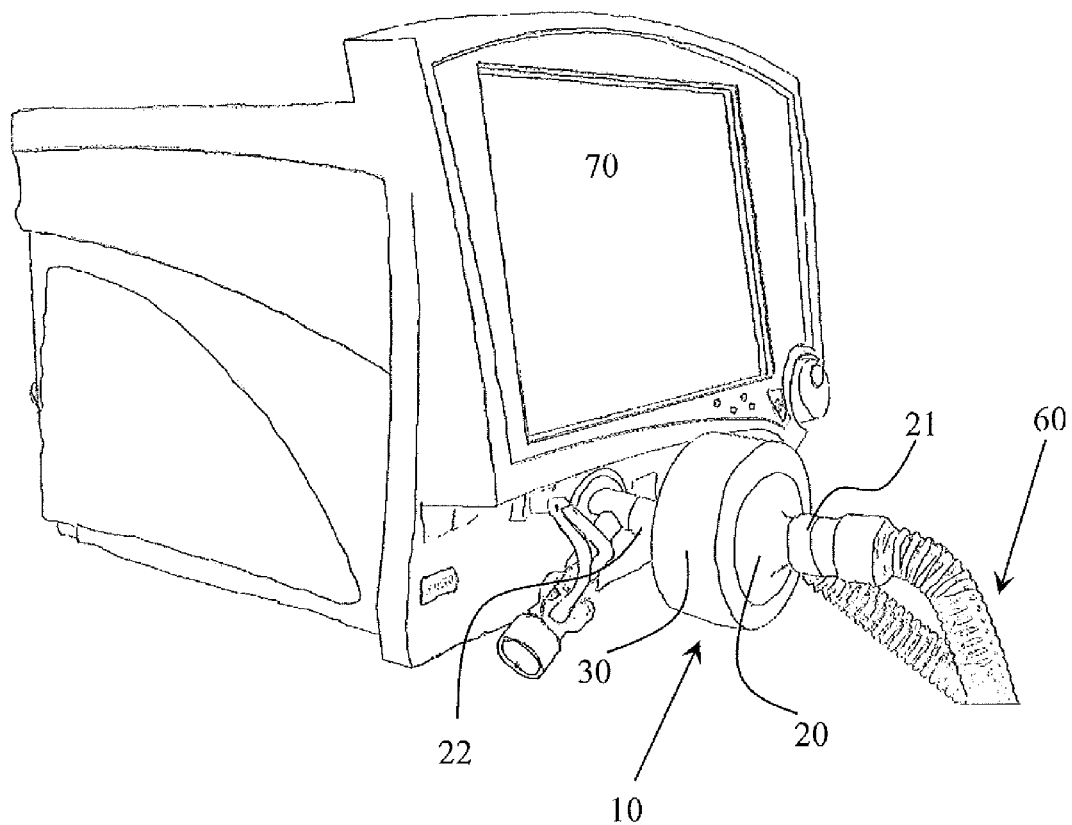
FIG. 1 is a perspective view illustrating of an exemplary heated filter system in line with an exhalation path of a ventilator system, in accordance with the present invention.

It is to be understood that the figures and descriptions of the present invention have been simplified to illustrate elements that are relevant for a clear understanding of the present invention, while eliminating, for the purpose of clarity, many other elements found in heated filter systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform, make or use the disclosed invention.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

The present invention includes a pathogen exhalation filter, and a system of heating said filter, used in conjunction with ventilator systems. However, while the present invention is generally described herein for use with ventilator systems, the present invention is not limited to such systems, and therefore can be designed and used for any type of system understood by those skilled in the art to include a heated filter. As used herein, the terms "filter system" or "filter assembly" refer to both a filter component and a filter heating component. These terms are used interchangeably hereinthroughout.

The exhalation circuit of ventilators provides components to monitor the exhaled air of a patient to assist and monitor a patient's breathing. As explained previously, exhaled air from the patient can cause the contamination of the surrounding air by bacteria exhaled from the sick patient. Further, because the exhaled air contains considerable moisture, the moisture can condense in the exhalation circuit. Condensate in the exhalation circuit can both damage the numerous components in the ventilator and serve as a pathogen breeding ground, thereby risking the functionality of the assisted breathing of the patient while at the same time exposing the patient or handler of the ventilator to unnecessary pathogen buildup.

The addition of a heated pathogen filter within the exhalation system can reduce contamination and the buildup of harmful condensate from exhaled air. Previous designed exhalation systems that include an external heated filter utilize a heating element that is always on and not safely regulated. The present invention provides a uniquely constructed pathogen filter that can reliably regulate the heating element, thereby increasing safety of the exhalation system. Therefore, unlike existing systems, wherein the heating element is either "always on" when the ventilator is on, or is controlled by a manual switch that is prone to be left on inadvertently, the present invention provides for a pathogen filter comprising an engagement ring, wherein electrical flow to power to the heating element is dependent on the engagement ring to close an electrical switch in the filter chamber.

As contemplated herein, the present invention includes a filter for keeping moisture in a vapor phase and removing particles from a gas. The filter includes a housing having a first opening and a second opening to create a passage therethrough, a filter medium contained within the housing and between the first opening and the second opening, such that a gas must pass through the filter medium along the passage, and a mechanical extension extending from the housing. The present invention also includes a system for keeping moisture in a vapor phase and removing particles from a gas. The system includes a heating chamber having a heating component and an electrical switch, a filter having a housing that includes a mechanical extension extending from the housing, wherein the filter is sized and shaped to engage the heating chamber, and wherein, when the filter engages the heating chamber, the mechanical extension closes the electrical switch of the heating chamber to activate heating of the filter.

The present invention also includes a method for keeping moisture in a vapor phase and removing particles from a gas. The method includes the steps of providing a heating chamber having a heating component and an electrical switch, providing a filter having a housing that includes a mechanical extension extending from the housing, wherein the filter is sized and shaped to engage the heating chamber, engaging the filter with the heating chamber, such that the mechanical extension closes the electrical switch of the heating chamber to activate heating of the filter, and administering a gas to the filter when the filter is heated, such that moisture is kept in a vapor phase and particles in the gas are captured in the filter. The methods of the present invention generally include use of any of the structural components of the filter system as described hereinthrought, and particularly for use with a ventilator system as would be understood by those skilled in the art.

In one embodiment, the present invention can be used as a heated bacteria filter in an exhalation path of a ventilator system. For example, FIG. 1 depicts the bacteria filter and heating filter chamber of the invention as an external filter system, distally connected to the exhalation path and proximally connected to the control unit of a mechanical ventilator system. As contemplated herein, the mechanical ventilation system can be any known in the art. Such mechanical ventilation systems include but are not limited to transport ventilators, intensive-care ventilators, neonatal ventilators, and positive airway pressure ventilators. Specific examples of suitable ventilator systems include, without limitation, the CareFusion Vela® ventilator. Further, the present invention can be used with any mode of ventilation known in the art. Modes of ventilation include but are not limited to controlled mechanical ventilation, volume controlled continuous mandatory ventilation, volume controlled intermittent mandatory ventilation, pressure controlled continuous mandatory ventilation, pressure controlled intermittent mandatory ventilation, high frequency ventilation, pressure support ventilation, and continuous positive airway pressure.

According to an aspect of the present invention and as shown generally in FIG. 1, the present invention includes a filter assembly 10, which comprises a bacteria filter 20 inserted into a filter heating chamber 30. In one embodiment, the assembly 10 is connected to the exhalation path of the ventilation circuit. As such, filter 20 comprises a proximal inlet or connecter 21 and a distal outlet or connector 22, wherein proximal connector 21 connects filter assembly 10 to the ventilation circuit 60, and distal connector 22 connects filter assembly 10 to the ventilator control and monitoring unit 70. In one embodiment, the filter system of the present invention is incorporated externally to a ventilation system where ventilation circuit 60 is a dual limb (double limb) circuit which includes an inhalation path and exhalation path. In this instance, ventilation circuit 60 is attached to the patient such that the exhaled air from the patient passes through the exhalation path and to filter assembly 10. In another embodiment, the tubing of ventilation circuit 60 is corrugated flexible tubing, wherein the tubing is either disposable or sterilizable, as would be understood by those skilled in the art. Materials used to form the flexible tubing include but are not limited to silicone rubber, high-density polyethylene, HYTREL™, and KRATON™. The design of the invention is not limited to the direction or orientation of filter 20, chamber 30, inlet 21 or outlet 22 in the ventilation circuit. Thus, in one embodiment inlet 21 and outlet 22 are reversed such that outlet 22 is connected to circuit 60 and inlet 21 is connected to monitoring unit 70.

As mentioned previously, ventilation circuit 60 is attached to filter assembly 10, through proximal connector 21. The connection between ventilation circuit 60 and proximal inlet 21 may be secured by standard attachment mechanisms as would be understood by those skilled in the art. Similarly, the proximal connection between distal outlet 22 and monitoring unit 70 is secured by standard attachment mechanisms suitable to the ventilator system used. It should be appreciated that monitoring unit 70 will vary according to the ventilator system used, and will include all necessary components to monitor the properties of exhaled air, such as flow, volume and pressure.

Figure 2:
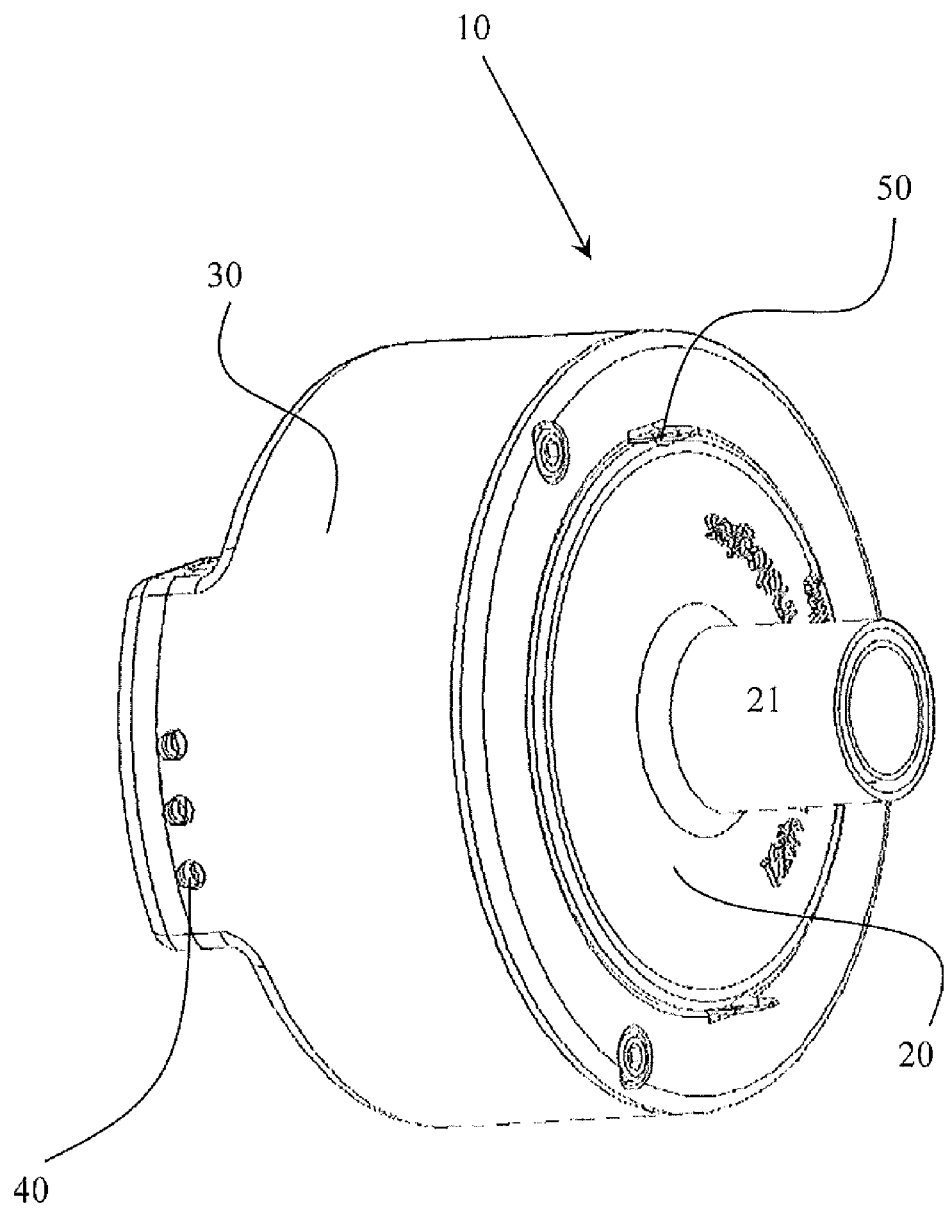
FIG. 2 is a perspective view of an exemplary heated pathogen filter assembly, comprising the filter inserted into the heating chamber, in accordance with the present invention.

FIG. 2 depicts filter assembly 10, comprised of filter 20 inserted into heating chamber 30. In one embodiment, filter 20 is inserted through a distal opening of heating chamber 30. In another embodiment, filter 20 may alternatively be inserted through a proximal opening of heating chamber 30.

As illustrated herein, heating chamber 30 may further include signal lights 40 which are used to indicate the function of heating chamber 30. As a non-limiting example, signal lights 40 may be light emitting diodes (LED) which are lit with various colors to distinguish filter conditions or functionality. For example, a green color light might be used to indicate when the chamber is powered and filter 20 is inserted properly, while a red color light might be used to indicate that power is fed to heating chamber 30, but the temperature is not at a suitable level. It should be appreciated that any number and combination of lights, or any other signally mechanism as would be understood by those skilled in the art, can be used to effectively convey assembly function and/or heating conditions of heating chamber 30.

Further, filter assembly 10 may include retention clips 50. In one embodiment, clips 50 are used to retain filter 20 when inserted within heating chamber 30. As contemplated herein, any number of clips can be used to effectively lock or otherwise prevent filter 20 from inadvertently slipping out of the chamber 30. In another embodiment, additional or separate locking elements can be used to secure filter 20 within heating chamber 30. As a non-limiting example, the distal edge of the heating chamber may be threaded, and a circular locking element or cap (not shown) can be fit over top the distal portion of the filter assembly to engage and rotate about the threads to lock the cap over the filter. It should be appreciated that any sort of locking mechanism as would be understood by those skilled in the art may be used to secure the filter to the heating chamber, or otherwise hold it in place when it its operative position.

Figure 3:
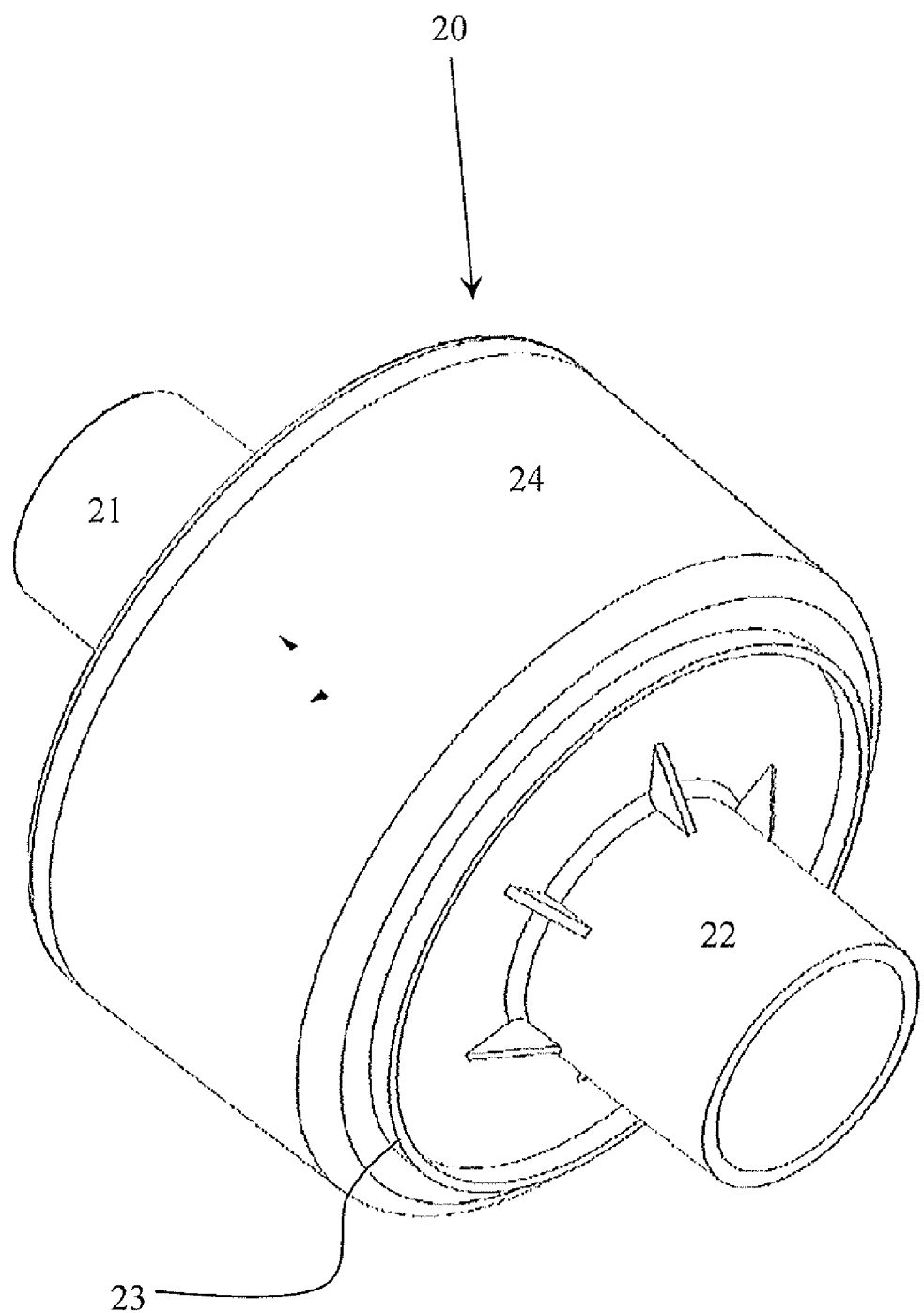
FIG. 3 is a perspective view of an exemplary pathogen filter, in accordance with the present invention.

FIG. 3 depicts filter 20 comprising distal outlet 22, proximal inlet 21, an engagement ring 23, and a filter housing 24. Filter 20 is encased in any suitable material that can withstand elevated temperatures of at least about 70° C. Materials include but are not limited to polyvinyl chloride and polycarbonate. In one embodiment, filter 20 is disposable. In another embodiment, filter 20 is reusable and sterilizable. Exhaled air passes through the exhalation path of ventilator circuit 60 to filter 20 through proximal inlet 21. As contemplated herein, inlet 21 may be of any dimension to form connections to the exhalation path suitable for the ventilator system incorporated therewith. Typically, inlet 21 and outlet 22 may include diameters measuring at International Standards Organization requirements of 22 mm taper outside diameter and 22 mm taper inside diameter respectively although other diameters may be used. For example, in one embodiment, inlet 21 has an outer diameter of about 22 mm. In another embodiment, inlet 21 has an inner diameter of about 15 mm.

As exhaled air passes through the filter, filtration substantially removes particles from the air. Removed particles include but are not limited to bacteria and viruses. As contemplated herein, any filtering mechanism as understood by those skilled in the art can be used and is housed within a housing 24 of filter 20. For example, filter 20 may include a mat of randomly arranged fibers, such as fiberglass fibers of between 0.2 and 2 micrometers in diameter. As with any filter medium, the fiber diameter, filter thickness and face velocity can all be manipulated to create the filtering of whatever particulate size desired. For example, in one embodiment, filtration of the exhaled air is performed through a HEPA filter within filter housing 24. In another embodiment, filtration is performed through a filter that is not HEPA rated, In one embodiment, filtration removes particles greater than about 0.5 microns. Preferably, filtration removes particles greater than about 0.4 microns. More preferably, filtration removes particles greater than about 0.3 microns. In one embodiment, filtration removes 99% of bacteria and virus particles, More preferably, filtration removes 99.9% of bacteria and virus particles. In one embodiment, the filter provides a resistance of flow of less than about 2.5 cm $H_2O$ at 100 L/min. After filtration, filtered exhaled air passes through distal outlet 22 to monitoring unit 70 of the ventilation system. Similar to inlet 21, outlet 22 may be of any dimension suitable to form connections to monitoring unit 70, As described elsewhere herein, the design of the invention is not limited by the direction or orientation of filter 20, chamber 30, inlet 21 and outlet 22.

As illustrated herein, filter 20 further comprises an engagement ring 23. Ring 23 serves to engage and mechanically close a switch (described below), In one embodiment, filter 20 is inserted into the distal opening 37 of heating chamber 30 (FIG. 4), such that ring 23 engages heating chamber 30 as described below. While ring 23 is primarily described and illustrated herein as being annular, it should be appreciated that there is no limitation to the shape or profile of ring 23, meaning ring 23 may alternatively be any shaped mechanical extension, such as a pin, wedge or any other shaped protrusion suitable for closing a switch within the heating chamber. Further still, ring 23 may include multiple protrusions to reflect different engagement points within the heating chamber.

Figure 4:
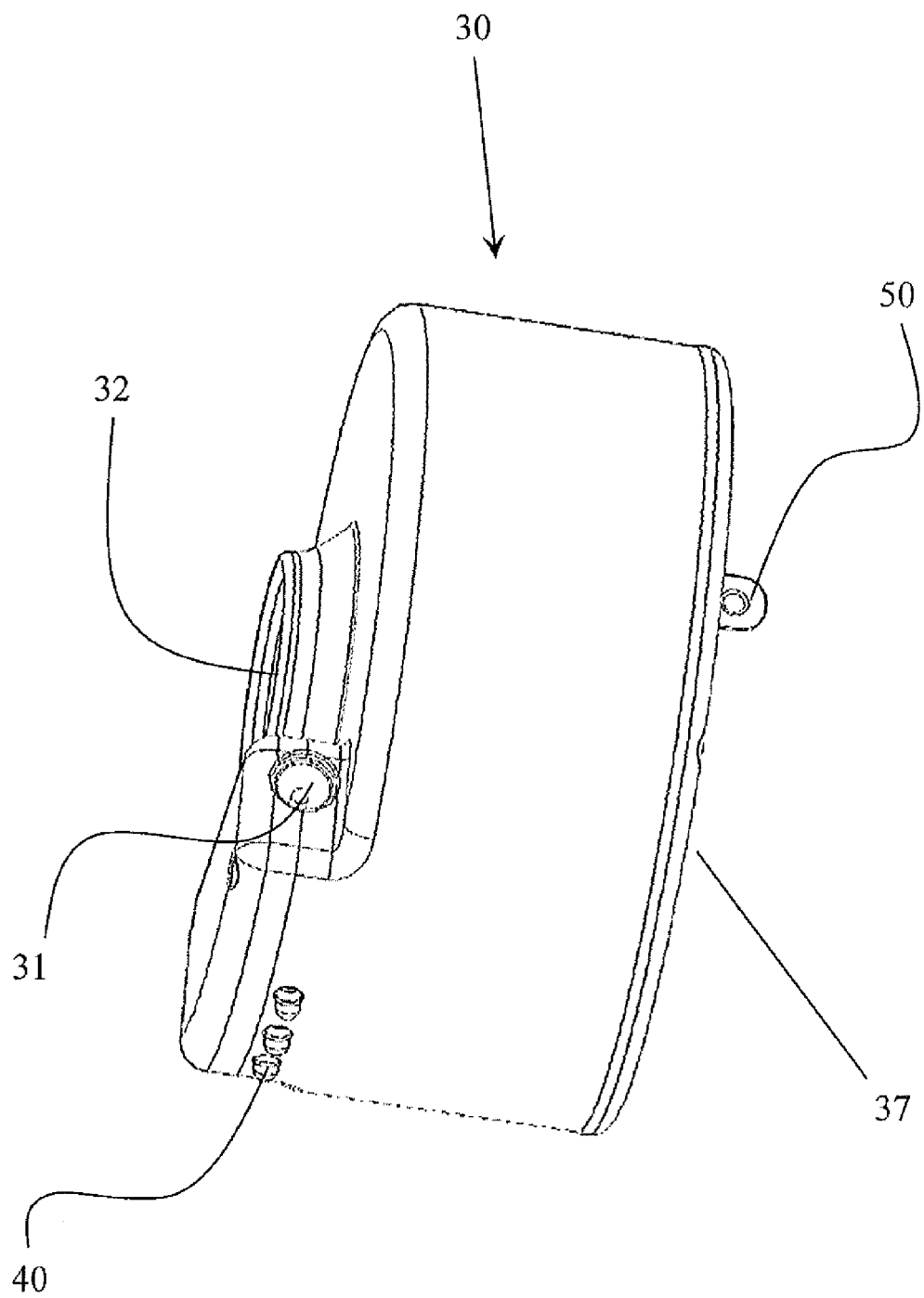
FIG. 4 is a perspective view of an exemplary heating chamber, in accordance with the present invention.

FIG. 4 depicts heating chamber 30 of the present invention, generally comprising a power connector 31, a distal opening 32, signal lights 40, and retention clips 50, Heating chamber 30 is sized and shaped to receive and snugly fit filter 20, when filter 20 is inserted through proximal opening 37 of heating chamber 30, and with outlet 22 of filter 20 extending through (or accessible through) distal opening 32 of heating chamber 30. Power to heating chamber 30 is supplied through the power connector 31 which connects heating chamber 30 to an external power supply via a standard power line. Alternatively, heating chamber 30 can include an internal battery, or it can be hard wired to a power source that forms part of or is separate from, the ventilator system. As would be understood by those skilled in the art, any power supply capable of delivering power to the chamber may be used. Such power supplies include but are not limited to a building's electrical network or an external battery that forms part of, or is separate from, the ventilator system. Connector 31 is of any type that can accept a suitable power cord from the external power supply. As a non-limiting example, connector 31 can be female coaxial power plug that accepts a male coaxial power jack. It should be understood that many other DC or AC connectors known in the art may be used.

Figure 5:
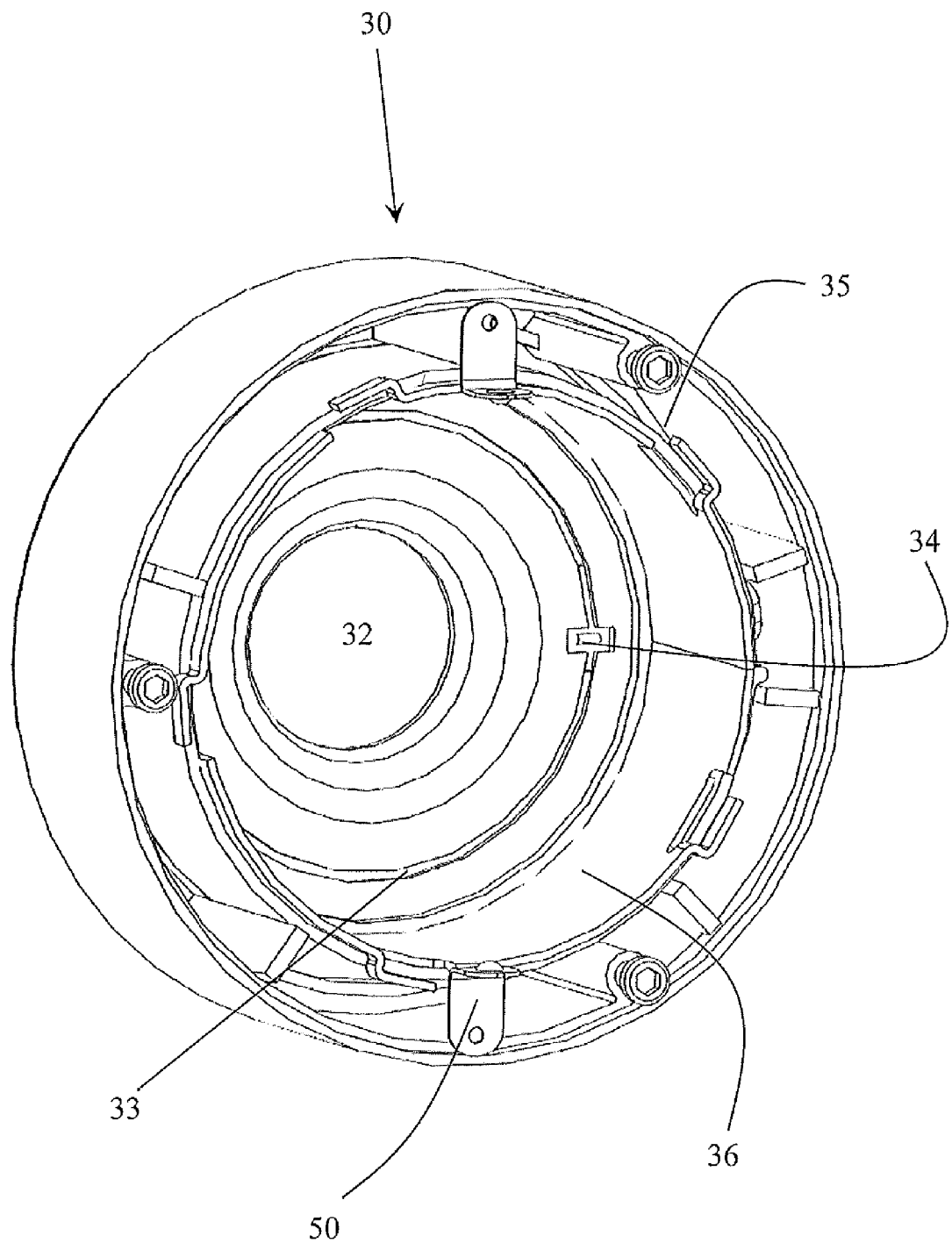
FIG. 5 is a perspective view of the inside of the heating chamber of FIG. 4, in accordance with the present invention.
Figure 6:
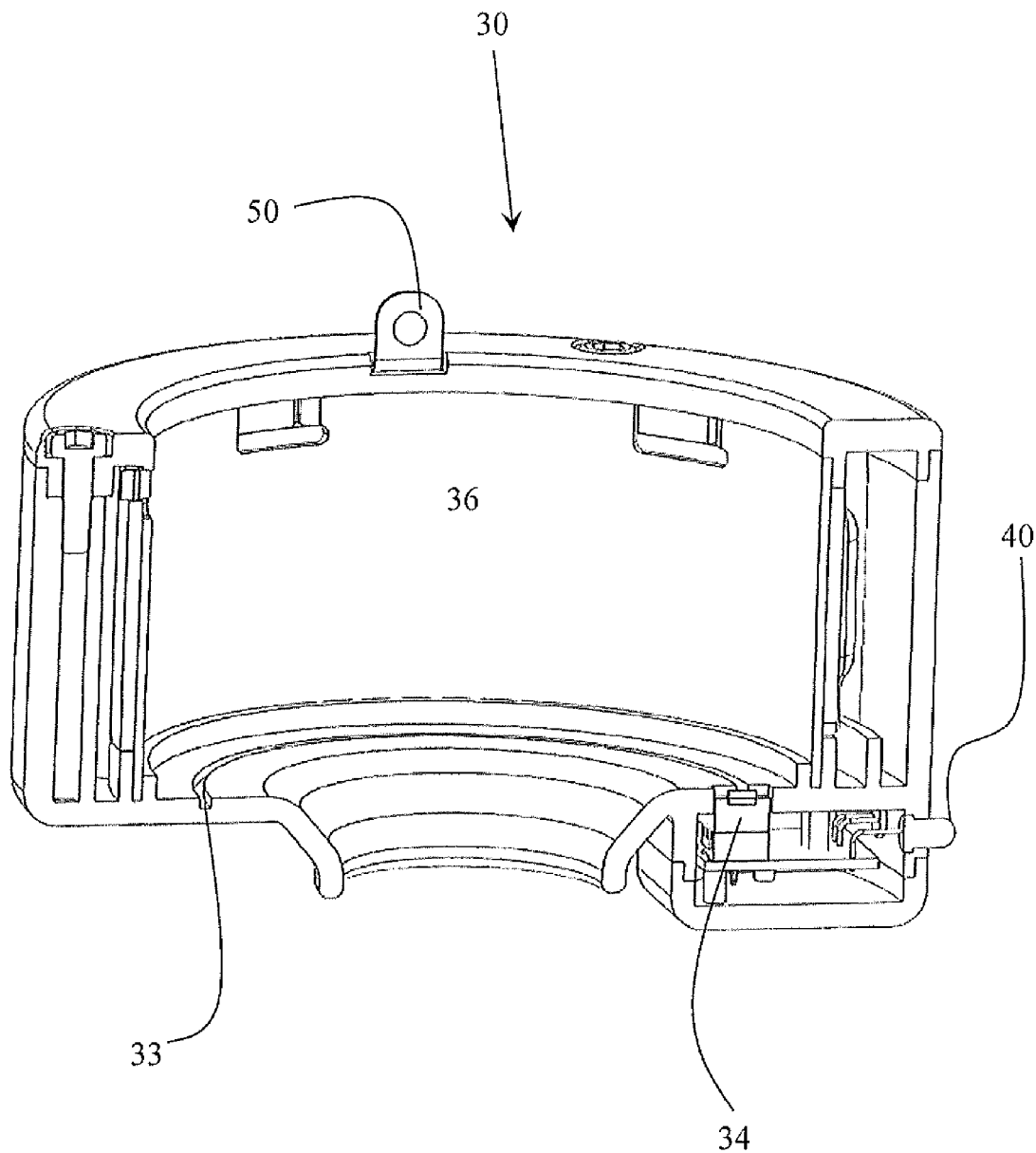
FIG. 6 is a cross-sectional view of the heating chamber of FIG. 4, in accordance with the present invention.
Figure 7:
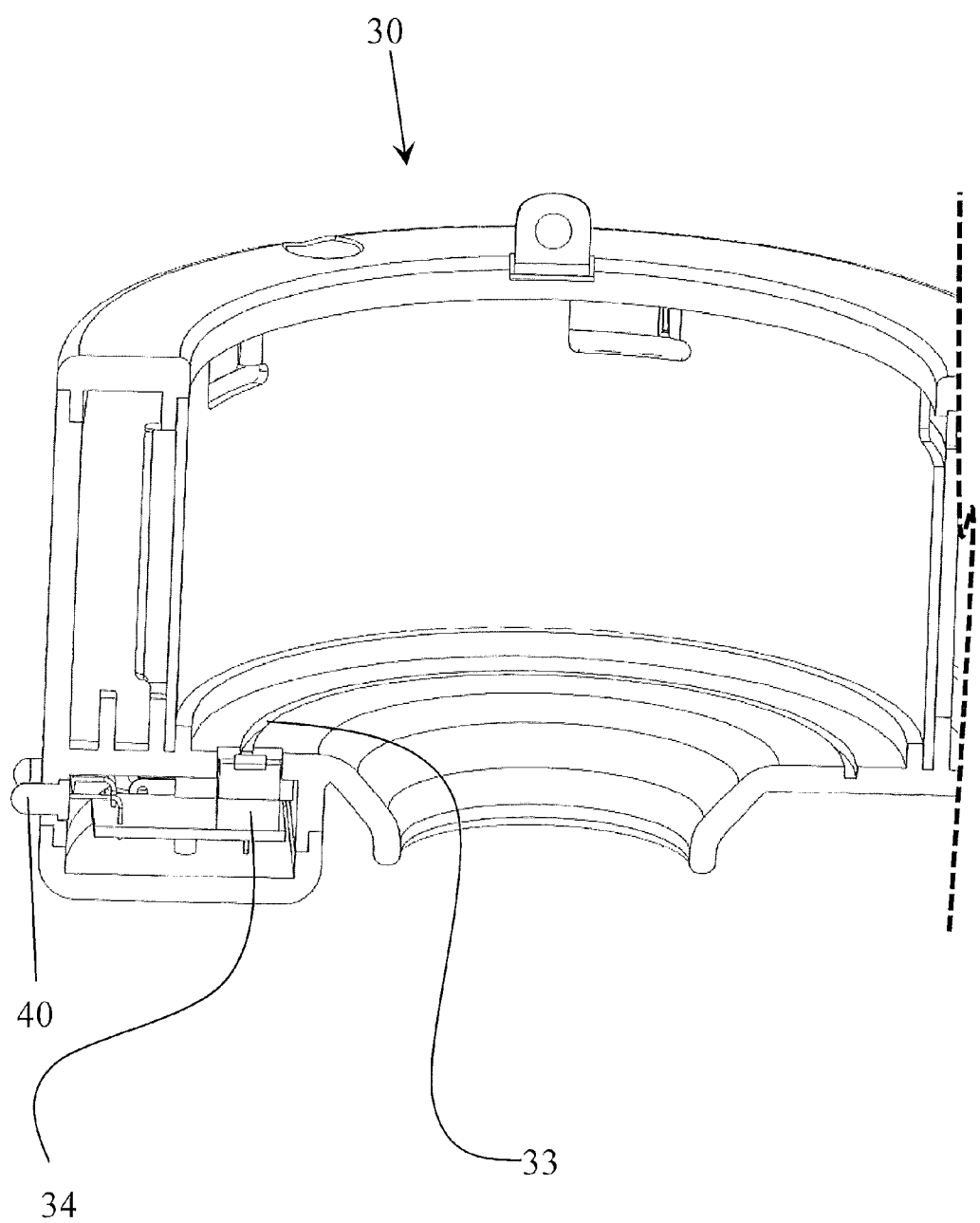
FIG. 7 is a cross-sectional view of the heating chamber of FIG. 4, in accordance with the present invention, depicting an exemplary recessed groove and switch used to power the heating chamber.

FIGS. 5-7 illustrate the internal mechanism of heating chamber 30. As depicted in FIGS. 5-7, heating chamber 30 further comprises a recessed groove 33, a recessed electrical switch 34, a heating element 35, a metal heat transfer plate 36 and electrical circuitry electrically connecting connector 31 to the aforementioned electrical components, including lights 40, as would be understood by those skilled in the art. When heating chamber 30 is alone, or separated from filter 20, switch 34 is open, thereby prohibiting the passage of electrical current from connector 31 to heating element 35 and heat transfer plate 36. Upon the insertion of filter 20, ring 23 substantially fits within and engages groove 33 of heating chamber 30, providing sufficient contact to mechanically close electrical switch 34 to enable current to be supplied to heating element 35 and/or transfer plate 36. When ring 23 is a continuous, annular protrusion, such as illustrated in the embodiment of FIG. 3, filter 20 is not "positionally restricted" when engaging heating element 30. In other words, because ring 23 is an annular protrusion, it can effectively engage recessed groove 33 and close switch 34 at any degree of rotation about a central axis of filter 20. This feature provides an additional ease-of-use for an operator of the filter assembly and ventilation system, in that the operator does not need to "line up" filter 20 in a particular position in order for ring 23 to engage and close switch 34. In alternative embodiments where full or partial positional restriction is desired, or depending on the type of switch 34 used, ring 23 may be discontinuous, such as a segmented annular protrusion, or it may be a pin, wedge or any other shape suitable for engaging and closing switch 34.

As would be understood by those skilled in the art, switch 34 may include any sort of electromechanical configuration that permits for current to flow through the switch when filter 20 is operably fitted within heating chamber 30. As a non-limiting example, switch 34 may include a push-button switch that is a normally open (NO) switch, otherwise known as a "push-to-make" switch, wherein the depressing of the switch, in this case by inserting ring 23 into groove 33, engages the switch to allow current flow. In this example, release of the switch by removing ring 23 from groove 33, breaks the circuit and prevents current flow to heating element 35. Other switches known in the art which may be used in the present invention include but are not limited to a miniature snap-action switch, a capacitance touch switch, resistance touch switch, an optical switch, and a reed switch. No matter what sort of electrical switch is used, the present invention provides for the regulation of heating of chamber 30 to occur only when filter 20 is operatively engaged within it.

When filter 20 is inserted into heating chamber 30 such that ring 23 engages groove 33 to close switch 34, electrical current is permitted to flow to heating element 35 and initiate heat production. As would be understood by those skilled in the art, the heating element of the invention may be any heating element known in the art. Non-limiting examples of heating elements include resistance wire, strip heating elements, Calrod™, etched foil heaters, and band heating elements. Resistance wire may be formed in any shape and can comprise wires comprised of Kanthal, Nichrome, Cupronickel, or other suitable materials. Heat produced by element 35 is applied to heat transfer plate 36, which in turn transfers heat to the inserted filter 20 snugly contacting transfer plate 36. Plate 36 may be formed from any conductive material. Examples of conductive materials include but are not limited to aluminum, brass, copper, gold, magnesium, silver, tungsten, stainless steel, iron, and platinum. In certain embodiments, heating element 35 and transfer plate 36 may be integrated into a single component. The temperature of plate 36, when heated, must be suitable for transferring enough heat to filter 20 suitable for the ventilator system requirements. For example, in one embodiment, the temperature is maintained between 40° C. to 70° C. In another embodiment, the temperature is maintained between 45° C. to 65° C. In the preferred embodiment, the temperature is maintained between 50° C. to 60° C.

In one embodiment, chamber 30 may further comprise a thermoswitch which provides for protection from overheating. In another embodiment, the chamber comprises an audio alarm, wherein the alarm is triggered in the event of, for example, overheating of the chamber or the failure to heat the chamber. Further, in another embodiment, heating element 35 and transfer plate 36 may be surrounded by a molded nonconductive material to prevent excessive heating of the outer surface of the chamber 30. In another embodiment, a capacitor charged by power to the heating element keeps a light 40 illuminated once power has been removed, wherein the duration of the illumination of light 40 is relative to the time for the transfer plate temperature to decrease to a safe to touch level.

As described herein, insertion of filter 20 into chamber 30 to form filter assembly 10 activates heating element 35 of the chamber such that heat transfer plate 36 transfers heat to inserted filter 20. As such, the heating of filter 20 is reliably regulated and controlled such that heating only occurs when the filter is operably positioned within the assembly, thereby providing a safer and more efficient heated pathogen filter. Likewise, the present invention provides a simple "shut-off" functionality, in that the heater is automatically shut off when a user of the present invention disengages the filter from the assembly.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A system for keeping moisture in a vapor phase and for removing particles from a gas, comprising:

a heating chamber having a heating component and an electrical switch;

a filter having a housing that includes a mechanical extension extending from the housing, wherein the filter is sized and shaped to engage the heating chamber;

wherein, when the filter engages the heating chamber, the mechanical extension closes the electrical switch of the heating chamber to activate heating of the filter.

2. The system of claim 1, wherein the mechanical extension is an annular ring.

3. The system of claim 1, wherein the heating component comprises a heating element and a heat transfer plate.

4. The system of claim 1, wherein the filter is heated between about 40° C. and 70° C.

5. The system of claim 1, wherein the filter is a HEPA filter.

6. The system of claim 1, wherein the filter is a bacterial filter for a ventilator.

7. The system of claim 1, wherein the gas is an exhaled gas from a ventilated subject.

8. A method for keeping moisture in a vapor phase and for removing particles from a gas, comprising:

providing a heating chamber having a heating component and an electrical switch;

providing a filter having a housing that includes a mechanical extension extending from the housing, wherein the filter is sized and shaped to engage the heating chamber;

engaging the filter with the heating chamber, such that the mechanical extension closes the electrical switch of the heating chamber to activate heating of the filter; and administering a gas to the filter when the filter is heated, such that moisture is kept in a vapor phase and particles in the gas are captured in the filter.

9. The method of claim 8, further comprising heating the filter between about 40° C. and 70° C.

10. The method of claim 8, wherein the filter is a HEPA filter.

11. The method of claim 8, wherein the gas is an exhaled gas from a ventilated subject.

* * * * *